United States Patent [19]

Tolman et al.

[11] Patent Number: 4,782,062

[45] Date of Patent: Nov. 1, 1988

[54] 9-(2-HYDROXYMETHYL)CYCLOALKYL-METHYL) GUANINES

[75] Inventors: Richard L. Tolman, Warren, N.J.; John D. Karkas, New York, N.Y.; Wallace T. Ashton, Clark, N.J.

[73] Assignee: Merck & Co., Inc., Rahway, N.J.

[21] Appl. No.: 48,289

[22] Filed: May 11, 1987

[51] Int. Cl.$^4$ .................... C07D 473/18; A61K 31/52
[52] U.S. Cl. .................................. 514/262; 514/261; 544/276; 544/277
[58] Field of Search ...................... 544/276, 277, 267; 514/262, 261

[56] References Cited

U.S. PATENT DOCUMENTS 4,617,304  10/1986  Ashton et al. ................... 544/277

Primary Examiner—Nicholas S. Rizzo
Attorney, Agent, or Firm—Richard S. Parr; Hesna J. Pfeiffer

[57] ABSTRACT

9-[2-(Hydroxymethyl)cycloalkylmethyl]guanines which are herpes simplex viral thymidine kinase inhibitors, their acyl derivatives, their phosphate derivatives and their pharmaceutically-acceptable salts; pharmaceutical formulations containing these compounds; the treatment of DNA viral, particularly herpes viral, infections with these compounds; methods of preparing these compounds; and novel intermediates useful in their preparation.

6 Claims, 6 Drawing Sheets

9-(2-HYDROXYMETHYL)CYCLOALKYL-METHYL) GUANINES

BACKGROUND OF THE INVENTION

The use of purine derivatives as anti-viral compounds is known. For example, U.S. Pat. No. 4,027,025 discloses 8-azapurine derivatives, such as 9-(2-hydroxyethoxymethyl)-8-azaguanine and 9-(2-benzoyloxyethoxymethyl)-8-azaguanine, as anti-viral compounds. U.S. Pat. No. 4,146,715 discloses 2-amido-9-(2-acyloxyethoxymethyl)hypoxanthines, and U.S. Pat. No. 4,199,574 discloses that 9-(2-hydroxyethoxymethyl) and related derivatives of certain 6-, and 2,6-substituted purines have anti-viral activity. U.S. Pat. Nos. 4,347,360 and 4,355,032 disclose that 9-[[2-hydroxy-1-(hydroxymethyl)ethoxy]methyl]guanine (gancyclovir) has anti-viral activity and Colla et al., *J. Med. Chem.*, 26, 602–604 (1983) and published European Patent Application No. 95 813 disclose esters or esters and ethers of acyclovir. European Patent Application Publication No. 85 424 discloses acyl derivatives of 9-(1,3-dihydroxy-2-propoxymethyl)guanine and U.S. Pat. No. 4,617,304 discloses thymidine kinase substrates having a 3-membered cycloalkyl group in the side chain of a purin-9-yl or pyrimidin-1-yl derivative, but disclose these compounds only as anti-viral agents, not as viral thymidine kinase inhibitors.

Inhibition of herpes simplex type I (HSV-1) thymidine kinase by certain 9-(hydroxyalkyl)- and 9-(hydroxyalkenyl)guanines has been disclosed in published EPO Application No. 146 516, but the antiviral activity of the compounds disclosed has been attributed to selective phosphorylation by the HSV thymidine kinase and subsequent inhibition of the viral DNA polymerase (A. Larsson et al, *Antimicrob. Agents Chemother.*, 30, 598–605 (1986)).

Herpes simplex virus infections are currently best treated with acyclovir (ACV), which is a selective *substrate* for HSV thymidine kinase and (as the triphosphate) inhibits HSV DNA polymerase. ACV does not prevent establishment of latent infection, however, and for prophylaxis of recurrent infection, it must be administered daily in high doses. The maximum course of such treatment approved by the FDA is 6 months, after which the recurrences return to normal frequency.

Known antiviral agents, such as acyclovir, gancyclovir and BVDU, however, are susceptible to enzymatic phosphorylation in non-infected cells to a small extent and thus have an effect upon nucleotide pool sizes and, by means of DNA polymerase, can be incorporated into DNA, thus raising mutagenicity hazards.

It is believed that non-TK-substrates, which might not possess chemotherapeutic efficacy, would have potential in the prevention of viral reactivation from latency or in the abolition of viral latency itself.

It was therefore an object of the present invention to identify novel, viral thymidine kinase (TK) inhibitory compounds which are not TK-substrates. Another object was to identify compounds which have utility and particularly safety in the treatment of specific members of the herpes group (i.e., herpes simplex, types 1 and 2, and varicella zoster), which express their own thymidine kinase. A further object of the present invention was to identify pharmaceutical formulations for the effective administration of the novel compounds of the invention. Still another object is to provide methods for the preparation of the novel compounds of the present invention.

DESCRIPTION OF THE INVENTION

The present invention relates to herpes simplex viral thymidine kinase inhibitors and, more particularly, to 9-[2-(hydroxymethyl)cycloalkylmethyl]-8-substituted-guanines of formula I:

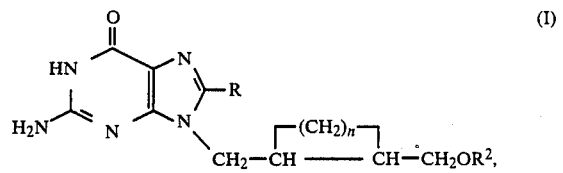

wherein R is H, halogen, $C_1$–$C_4$-straight or branched-chain alkyl, 2-halovinyl, or 2-haloethyl;

$R^2$ is H or

wherein $R^1$ is a straight- or branched-chain alkyl group of 1 to 12 carbon atoms, or phenyl or naphthyl;

and n is 2 to 6;

and to pharmaceutically-acceptable salts thereof.

Both the E and Z isomers, each of which is a pair of enantiomers, of which one enantiomer may be a better inhibitor than its antipode, are included in these definitions.

Preferred compounds according to the present invention include:

9-[(Z)-2-(hydroxymethyl)cyclobutylmethyl]guanine;
9-[(Z)-2-(hydroxymethyl)cyclopentylmethyl]guanine;
9-[(Z)-2-(hydroxymethyl)cyclohexylmethyl]guanine;
9-[(E)-2-(hydroxymethyl)cyclohexylmethyl]guanine;
9-[(Z)-2-(hydroxymethyl)cycloheptylmethyl]guanine;
9-[(Z)-2-(hydroxymethyl)cyclooctylmethyl]guanine;
9-[(Z)-2-(propionyloxymethyl)cyclohexylmethyl]guanine;
9-[(Z)-2-(benzoyloxymethyl)cyclohexylmethyl]guanine; and
9-[(Z)-2-(acetoxymethyl)cyclohexylmethyl]guanine.

Particularly preferred compounds according to the present application then include:

9-[(Z)-2-(hydroxymethyl)cyclohexylmethyl]guanine;
9-[(Z)-2-(hydroxymethyl)cyclobutylmethyl]guanine; and
9-[(Z)-2-(hydroxymethyl)cyclopentylmethyl]guanine.

The compounds discloses herein have biological or chemical properties which give them advantages in the treatment of the various diseases and ailments associated with members of the herpes group of viruses which express their own thymine kinases, and which are safe to use, particularly in the treatment of latent infections. Furthermore, the corresponding acyl derivatives of the compounds of Formula I are preferred because they have formulation and pharmacodynamic advantages, that is, the acyl group can impart aqueous or oil solubility which is an asset in oral or topical formulation and can facilitate intestinal uptake or passage through the stratum corneum and can also act to extend plasma half-life.

The compounds of formula I may be prepared, in most general terms, by alkylation of a protected guanine or guanine precursor with a protected 2-(hydroxymethyl)cycloalkylmethyl halide or arene- or alkanesulfonate, followed by deprotection using standard methods. One of the two hydroxyl groups of a cycloalkane-1,2-dimethanol is protected, e.g., by acylation with an equivalent of benzoyl chloride in the presence of a base such as pyridine. The remaining hydroxyl group is converted to a leaving group by standard methods, for example, it may be transformed to a bromo group with carbon tetrabromide and triphenylphosphine; to an iodo group with methyltriphenoxyphosphonium iodide; or to a p-toluenesulfonate group with p-toluenesulfonyl chloride in the presence of a base such as pyridine. Suitable protected guanines or guanine precursors include 2-amino-6-benzyloxypurine and 2-amino-6-chloropurine. The alkylation may be carried out at about 20°–120° C., typically 40°–90° C., in a variety of solvents, especially a polar, aprotic solvent such as N,N-dimethylformamide or dimethyl sulfoxide. A base such as sodium hydride is employed to generate the purine anion. Typically, a mixture of 9- and 7-alkylated isomers is obtained, and these are separated chromatographically. The purine $O^6$-benzyl group may be removed by various means, including treatment with anhydrous trifluoroacetic acid or catalytic hydrogenolysis. The side chain O-acyl group may also be removed by a variety of methods, including catalytic sodium methoxide in methanol, aqueous methylamine, or anhydrous ammonia in methanol. In the case of 2-amino-6-chloropurine derivatives, conversion to the guanine may be accomplished by standard hydrolytic methods, for example, simultaneous hydrolysis of the 6-chloro group and deacylation of the side chain can be achieved by heating with 2.5N hydrochloric acid at 100°.

The acyl derivatives are preferably prepared by reacting the compounds of formula I with the appropriate acyl halide, acid anhydride, or other activated acyl species in the presence of an appropriate cosolvent such as, for example, pyridine-dimethylformamide. In reaction with acyl halide or acid anhydrides the reaction rate and yield can be increased by the addition of a tertiary amine such as triethylamine, with 4-dimethylaminopyridine being an effective catalyst. Other activated acyl species may be prepared by reaction of the acid with a suitable activating agent such as, for example, 1,1'-carbonyldiimidazole, N,N'-dicyclohexylcarbodiimide or by acylation of N-hydroxysuccinimide or 1-hydroxybenzotriazole by known methods.

Compounds of the present invention are potent and specific inhibitors of herpes simplex viral thymidine kinase. As such, their toxicity to mammalian cells is minimal. These compounds additionally are resistant to enzymatic phosphorylation, even in virus-infected cells, and therefore, mutagenicity hazards are minimized, in that inhibition of DNA polymerase and incorporation into DNA are avoided. These compounds in effect mimic the thymidine kinase deficiency of TK⁻ mutants. HSV TK⁻ mutants tend to be less pathogenic, have diminished ability to establish latent infections, and may be incapable of reactivation if latent infection occurs [R. J. Klein, *Antiviral Res., Suppl.* 1, 111 (1985) and references therein]. The invention is intended for the treatment of prophylaxis of herpes (especially herpes simplex) virus infections in man and may be of particular utility in preventing recurrence of latent virus infection.

The compounds of the present invention may be administered to mammalian or avian species either individually or in combinations in dosage levels effective to impart a viral thymidine kinase-inhibiting activity. Typically such therapeutically-effective levels are from about 0.01 to about 200 mg/kg/day. The compounds of the present invention may be formulated according to accepted pharmaceutical practice for administration orally, topically or by injection according to known methods. Suitable oral dosage forms include tablets, capsules, elixirs or powders, while solutions or suspensions in, for example, phosphate buffered saline or water are suitable for injection. Examples of suitable topical formulations are gels, ointments, solutions or suspensions.

The following Examples illustrate the present invention without, however, limiting the same thereto. All temperatures are expressed in degrees Celsius.

EXAMPLE 1

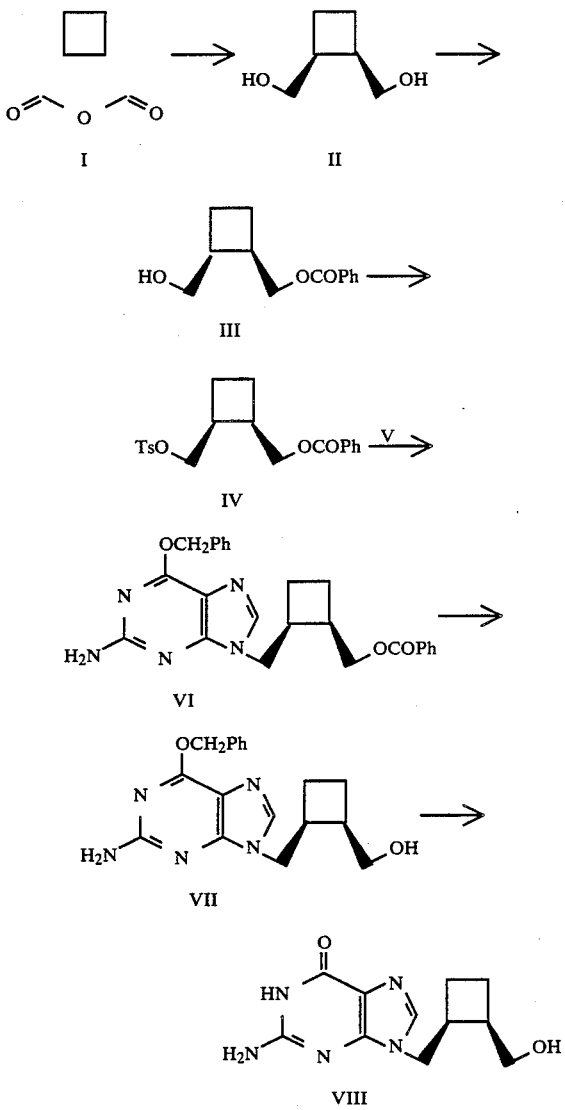

A. (Z)-2-(Benzoyloxymethyl)cyclobutanemethanol (III)

To a solution of 2.70 g (23.2 mmole) of (Z)-1,2-cyclobutanedimethanol [II, obtained by lithium aluminum hydride reduction of cis-1,2-cyclobutanedicarboxylic anhydride (I) as previously reported: W. J. Bailey, C. H. Cunov, and L. Nicholas, *J. Am. Chem. Soc.*, 77, 2787 (1955) and N. L. Allinger, M. Nakazaki, and V. Zalkow, *J. Am. Chem. Soc.*, 81, 4074 (1959)] and 2.35 ml of pyridine in 25 ml of $CH_2Cl_2$ stirred under nitrogen at 0° C. was added gradually 3.34 ml (3.27 g, 23.2 mmole) of benzoyl chloride. The mixture was stirred overnight at room temperature and then partitioned between ethyl acetate and water. The ethyl acetate phase was washed further with water, dried over magnesium sulfate, filtered, and concentrated in vacuo. The aqueous phase from the separation was extracted with ethyl acetate. The organic extracts were processed as above and combined with the original isolate. The evaporation residue was chromatographed on a column of 500 g. of silica gel packed in hexane. The column was eluted with a gradient of from 5% to 25% ethyl acetate in hexane, affording 2.00 g (39%) of the monobenzoylated product III as an oil. This material was homogeneous by TLC (2:1 hexane-ethyl acetate), and the structure was confirmed by NMR ($CDCl_3$).

B. (Z)-2-(Benzoyloxymethyl)cyclobutylmethyl p-toluenesulfonate (IV)

A solution of 1.17 g (5.3 mmole) of (Z)-2-(benzoyloxymethyl)cyclobutanemethanol (III) in 9 ml of pyridine was stirred in an ice bath under protection from moisture as 1.27 g (6.65 mmole) of p-toluenesulfonyl chloride was added portionwise. The mixture was stirred overnight at room temperature, then poured into icewater and extracted with ether. The ethereal layer was washed successively with water, 0.5N hydrochloric acid, and water. The ether solution was dried over magnesium sulfate, filtered, and concentrated in vacuo to give 1.62 g (82%) of the product as a viscous oil, which showed satisfactory purity by TLC (2:1 hexane-ethyl acetate). The structure was confirmed by NMR.

C. 2-Amino-9-[(Z)-2-(benzoyloxymethyl)cyclobutylmethyl]-6-benzyloxypurine (VI)

A solution of 907 mg (3.76 mmole) of 2-amino-6-benzyloxypurine (V) in 10 ml of dry dimethylformamide (DMF) was treated with 166 mg (4.14 mmole) of sodium hydride (60% in mineral oil). The mixture was stirred under nitrogen at ambient temperature. After 30 minutes, when hydrogen evolution had subsided and a clear solution had formed, a solution of 1.55 g (4.14 mmole) of (Z)-2-(benzoyloxymethyl)cyclobutylmethyl p-toluenesulfonate (IV) in 1 ml of DMF was added dropwise. The mixture was heated at 60° C. for 12 hours and then neutralized by addition of a few drops of glacial acetic acid. Concentration in vacuo gave a semisolid, which was taken up in ethyl acetate and filtered to remove insolubles. The residue from evaporation of the filtrate was chromatographed on a column of 200 ml of silica gel 60 packed in ethyl acetate. Elution with ethyl acetate afforded 620 mg (37%) of the desired product as an oil, homogeneous by TLC (ethyl acetate). The NMR ($CDCl_3$) was consistent with its assignment as a 9-alkylated purine derivative. (Note: a by-product which was eluted ahead of the product was tentatively identified as 2-amino-6-benzyloxy-9-(p-toluenesulfonyl)purine.)

D. 2-Amino-6-benzyloxy-9-[(Z)-2-(hydroxymethyl)cyclobutylmethyl]purine (VII)

A mixture of 580 mg (2.25 mmole) of 2-amino-9-[(Z)-2-(benzoyloxymethyl)cyclobutylmethyl]-6-benzyloxypurine (VI) and 10 ml of methanol was treated with small amounts of 1N sodium methoxide in methanol until strongly basic by pH paper. The mixture was heated on a steam bath for 45 minutes and then concentrated in vacuo. The residue was chromatographed on a column of 180 ml of silica gel packed in methylene chloride. Elution with 2% and then 5% methanol in methylene chloride afforded 365 mg (48%) of VII as white crystals, mp 144.5°–146° C. The material was homogeneous by TLC (9:1 chloroform-methanol), and its structure was confirmed by NMR ($CDCl_3$). (A minor by-product eluted subsequent to the product was identified by NMR as the corresponding 2-amino-6-methoxy purine.)

E. 9-[(Z)-2-(Hydroxymethyl)cyclobutylmethyl]guanine (VIII)

A mixture of 344 mg (1.01 mmole) of 2-amino-6-benzyloxy-9-[(Z)-2-(hydroxymethyl)cyclobutylmethyl]purine (VII), 50 mg of 20% palladium hydroxide on carbon, and 10 ml of methanol was shaken with hydrogen (approximately 40 psig) on a Parr apparatus. After 2 hours, when TLC (9:1 chloroform-methanol) indicated complete conversion of starting material to a product of lower $R_f$, the mixture was treated with 5 ml of water, heated on a steam bath, and filtered while hot through Celite. The filtrate was concentrated in vacuo, and trituration of the residue with water gave 81 mg of solid. The Celite-catalyst mixture was resuspended in water-methanol, heated, and worked up as above to provide an additional 41 mg of product. The total yield of white solid was thus 122 mg (49%), mp >315° C. (dec.). The material was homogeneous by TLC (9:1 chloroform-methanol), and the structure was verified by NMR (DMSO-$d_6$).

Elemental analysis Calcd. for $C_{11}H_{15}N_5O_2.0.2\ H_2O$: C, 52.25%; H, 6.14%; N, 27.70%. Found: C, 52.57%, H, 6.34%; N, 27.45%.

EXAMPLE 2

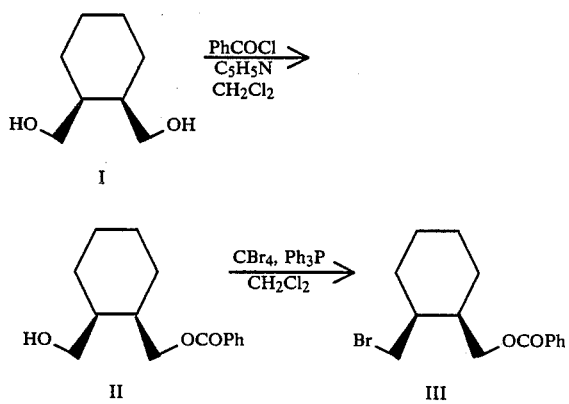

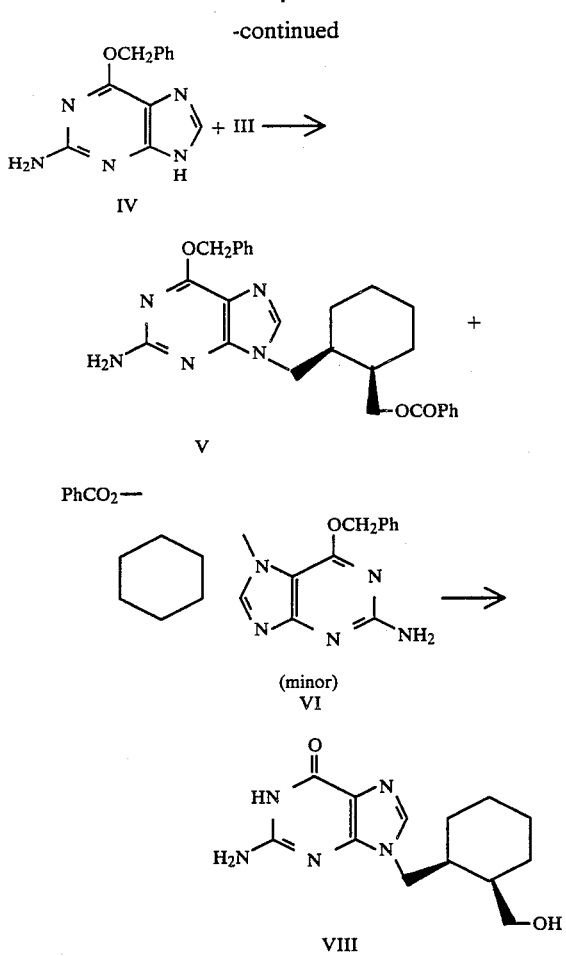

A. (Z)-2-(Benzoyloxymethyl)cyclohexanemethanol (II)

To a solution of 50.0 g (0.346 mole) of cis-1,2-cyclohexanedimethanol (I) and 35 ml of pyridine in 400 ml of methylene chloride stirred under nitrogen at 0° C. was added dropwise 40.25 ml (48.7 g, 0.346 mole) of benzoyl chloride. After completion of the addition, the mixture was allowed to warm to room temperature and was stirred overnight. The mixture was concentrated in vacuo, and the residue was partitioned between ethyl acetate and water. The organic layer was washed with water, then dried (MgSO$_4$), filtered and concentrated. The residual oil was chromatographed on a column of silica gel (elution with 9:1 hexane-ethyl acetate followed by 4:1 hexane-ethyl acetate) to give 43.9 g (51%) of the product as an oil, which was homogeneous by TLC (9:1 hexane-ethyl acetate). The structure was confirmed by NMR (CDCl$_3$).

B. (Z)-2-(Benzoyloxymethyl)cyclohexylmethyl bromide (III)

A solution of 43.0 g (0.173 mole) of (Z)-2-(benzoyloxymethyl)cyclohexanemethanol (II) and 86.2 g (0.26 mole) of carbon tetrabromide in 400 ml of dry methylene chloride was stirred at room temperature as a solution of 54.3 g (0.207 mole) of triphenylphosphine in 100 ml of methylene chloride was added dropwise over a period of 2 hours. After 4 days of stirring at room temperature, TLC (4:1 hexane-ethyl acetate) indicated complete conversion of II to product (greater R$_f$). Concentration of the mixture gave a dark residue, which was triturated with 1:1 hexane-ethyl acetate. The insoluble solid was removed by filtration. The residue from concentration of the filtrate was chromatographed on a column of silica gel (elution with 99:1 and then 97:3 hexane-ethyl acetate), yielding 43.8 g (81%) of the product as an oil, which was homogeneous by TLC (9:1 hexane-ethyl acetate). The structure was confirmed by NMR and mass spectrum.

Elemental analysis. Calcd. for $C_{15}H_{19}BrO_2$: C, 57.89%; H, 6.15%; Br, 25.67%. Found: C, 58.03%; H, 6.16%; Br, 25.76%.

C. 2-Amino-9-[(Z)-2-(benzoyloxymethyl)cyclohexylmethyl]-6-benxyloxypurine (V)

A solution of 27.8 g (0.115 mole) of 2-amino-6-benxyloxypurine (IV) in 275 ml of dry dimethylformamide (DMF) was treated portionwise with 4.8 g (0.12 mole) of sodium hydride (60% in mineral oil). The mixture was stirred under nitrogen as hydrogen evolution proceeded, accompanied by a mild exotherm. Within 30 minutes, gas evolution had ceased and a clear, light amber solution had formed. This solution was then heated to 60°–65° C., as a solution of 39.4 g (0.126 mole) of (Z)-2-(benzyloxymethyl)cyclohexylmethyl bromide (III) in 30 ml of dry DMF was added dropwise. After completion of the addition, the mixture ws stirred for 19 hours at 60°, then cooled, and neutralized by addition of a few drops of glacial acetic acid. After concentration in vacuo (<5 mm), the residual solid was dissolved in 100 ml of methanol and evaporated onto 150 cc of silica gel 60. This was layered on top of a column of 2000 cc of silica gel 60 packed in methylene chloride. The column was eluted with 0.5% methanol and then 1% methanol in methylene chloride to isolate the desired 9-isomer (V), while the 7-isomer (VI) was eluted with higher concentrations (2–6%) of methanol. Fractions containing clean 9-isomer were combined and concentrated. Trituration of the residue with hexane yielded 11.5 g (21%) of white solid, mp 153°–154° C. Similar treatment of fractions containing clean 7-isomer (smaller R$_f$ by TLC in 19:1 methylene chloride-methanol) gave 8.8 g of white solid, mp 70°–72° C. Structural assignments were confirmed by NMR (CDCl$_3$) and mass spectrum.

Elemental analysis. Calcd. for $C_{27}H_{29}N_5O_3$: C, 68.78%; H, 6.20%; N, 14.86%. Found for the 9-alkylated isomer (V): C, 68.84%; H, 6.26%; N, 14.96%.

D. 9-[(Z)-2-(Benzoyloxymethyl)cyclohexylmethyl]guanine (VII)

To 10.63 g (22.5 mmole) of 2-amino-9-[(Z)-2-(benzoyloxymethyl)cyclohexylmethyl]-6-benzyloxypurine (V) was added 100 ml of trifluoroacetic acid. The flask was stoppered, and the solution was stirred for 2.5 hours, by which time TLC (9:1 chloroform-methanol) showed complete conversion to a product of lower R$_f$. The trifluoroacetic acid was evaporated in a stream of nitrogen. The residual oil was twice taken up in methanol and evaporated in a stream of nitrogen. Trituration of the residue with diethyl ether afforded a white solid, which was isolated on a filter and washed thoroughly with ether. Yield 8.36 g (97%), mp 315°–317° C. dec., homogeneous by TLC (9:1 chloroform-methanol). The structure was confirmed by NMR (DMSO-d$_6$).

Elemental analysis. Calcd. for $C_{20}H_{23}N_5O_3$: C, 62.98%; H, 6.08%; N, 18.36%. Found: C, 63.03%; H, 6.07%; N, 18.58%.

E. 9-[(Z)-2-(Hydroxymethyl)cyclohexylmethyl]guanine (VIII)

A suspension of 8.01 g (21 mmole) of 9-[(Z)-2-(benzoyloxymethyl)cyclohexylmethyl]guanine (VII) in 750 ml of methanol was treated with 40 ml (40 mmole) of freshly prepared 1M sodium methoxide in methanol. The mixture was stirred under nitrogen at room temperature for 6 days. By this time a homogeneous solution had resulted, and TLC (9:1 chloroform-methanol) indicated no unreacted starting material. The solution was neutralized with glacial acetic acid and concentrated in vacuo. Trituration of the residue with acetone gave a white solid. Upon recrystallization from water-methanol, a first crop of 3.45 g, mp 305°–307° C. dec., and a second crop of 1.56 g, mp 308°–309° C., were obtained. The total yield was 5.01 g (82%). The material was homogeneous by TLC (90:10:1 chloroform-methanol-water), and the structure was confirmed by NMR (DMSO-$d_6$).

Elemental analysis. Calcd. for $C_{13}H_{19}N_5O_2$. 0.75 $H_2O$: C, 53.68%; H, 7.10%; N, 24.08%. Found: C, 54.01%; H, 7.49%; N, 23.87%.

What is claimed is:

1. A 9-[2-(hydroxymethyl)cycloalkylmethyl]-8-substituted-guanine of the formula:

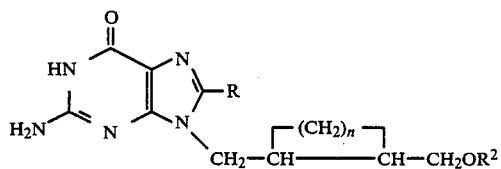

wherein R is H, halogen, $C_1$–$C_4$-straight or branched-chain alkyl; n is 2 to 6; and
$R^2$ is H or

wherein $R^1$ is $C_1$–$C_{12}$-straight or branched-chain alkyl, phenyl or naphthyl, or a pharmaceutically-acceptable salt thereof.

2. A 9-[2-(hydroxymethyl)cycloalkylmethyl]-8-substituted-guanine according to claim 1, which is
   9-[(Z)-2-(hydroxymethyl)cyclobutylmethyl]guanine;
   9-[(Z)-2-(hydroxymethyl)cyclopentylmethyl]guanine;
   9-[(Z)-2-(hydroxymethyl)cyclohexylmethyl]guanine;
   9-[(E)-2-(hydroxymethyl)cyclohexylmethyl]guanine;
   9-[(Z)-2-(hydroxymethyl)cycloheptylmethyl]guanine;
   9-[(Z)-2-(hydroxymethyl)cyclooctylmethyl]guanine;
   9-[(Z)-2-(propionyloxymethyl)cyclohexylmethyl]guanine;
   9-[(Z)-2-(benzyloxymethyl)cyclohexylmethyl]guanine; or
   9-[(Z)-2-(acetoxymethyl)cyclohexylmethyl]guanine.

3. A 9-[2-(hydroxymethyl)cycloalkylmethyl]-8-substituted-guanine according to claim 2, which is
   9-[(Z)-2-(hydroxymethyl)cyclohexylmethyl]guanine;
   9-[(Z)-2-(hydroxymethyl)cyclobutylmethyl]guanine; or
   9-[(Z)-2-(hydroxymethyl)cyclopentylmethyl]guanine.

4. A composition useful for imparting viral thymidine kinase-inhibiting activity comprising a carrier and a therapeutically-effective amount of a 9-[2-(hydroxymethyl)cycloalkylmethyl]-8-substituted-guanine according to claim 1.

5. A method of inhibiting viral thymidine kinase activity in mammalian or avian species comprising administering a therapeutically-effective amount of a 9-[2-(hydroxymethyl)cycloalkylmethyl]-8-substituted-guanine according to claim 1.

6. A method according to claim 5, wherein the viral thymidine kinase activity is a herpes viral thymidine kinase activity, the therapeutically-effective amount is from 0.01 to about 200 mg/kg of body weight/day, the mammalian or avian species is a human being, and the guanine according to claim 1 is
   9-[(Z)-2-(hydroxymethyl)cyclohexylmethyl]guanine;
   9-[(Z)-2-(hydroxymethyl)cyclobutylmethyl]guanine; or
   9-[(Z)-2-(hydroxymethyl)cyclopentylmethyl]guanine.

* * * * *

UNITED STATES PATENT AND TRADEMARK OFFICE
CERTIFICATE OF CORRECTION

PATENT NO. : 4,782,062

DATED : November 1, 1988

INVENTOR(S) : R.L. TOLMAN, J.D. KARKAS and W.T. ASHTON

It is certified that error appears in the above—identified patent and that said Letters Patent is hereby corrected as shown below:

IN THE TITLE:

Delete "9-(2-HYDROXYMETHYL)CYCLOALKYLMETHYL) GUANINES" and replace with -- 9-[2-(HYDROXYMETHYL)CYCLOALKYLMETHYL] GUANINES --.

Signed and Sealed this

Fourth Day of July, 1989

Attest:

DONALD J. QUIGG

Attesting Officer

Commissioner of Patents and Trademarks